United States Patent [19]

Miyano et al.

[11] Patent Number: 4,565,882
[45] Date of Patent: Jan. 21, 1986

[54] SUBSTITUTED DIHYDROBENZOPYRAN-2-CARBOXYLATES

[75] Inventors: Masateru Miyano, Northbrook; Robert L. Shone, Palatine, both of Ill.

[73] Assignee: G. D. Searle & Co., Skokie, Ill.

[21] Appl. No.: 568,846

[22] Filed: Jan. 6, 1984

[51] Int. Cl.[4] .......................................... C07D 311/04
[52] U.S. Cl. .................................. 549/399; 549/401; 549/402; 549/405
[58] Field of Search ................ 549/399, 402, 401, 405

[56] References Cited

U.S. PATENT DOCUMENTS

| | | | |
|---|---|---|---|
| 3,953,604 | 4/1976 | Warren et al. | 424/283 |
| 4,001,280 | 1/1977 | Umio et al. | 260/340.5 |
| 4,003,919 | 1/1977 | Scott et al. | 549/405 |
| 4,006,245 | 2/1977 | Augstein et al. | 424/283 |
| 4,153,614 | 5/1979 | Barner et al. | 549/405 |
| 4,156,726 | 5/1979 | Brown et al. | 424/258 |
| 4,213,903 | 7/1980 | Bantick et al. | 548/250 |
| 4,238,495 | 12/1980 | Warren et al. | 424/269 |
| 4,281,008 | 7/1981 | Chamberlain et al. | 424/269 |
| 4,328,230 | 5/1982 | Brown et al. | 424/256 |

FOREIGN PATENT DOCUMENTS

| | | | |
|---|---|---|---|
| 0079637 | 5/1983 | European Pat. Off. | 549/601 |
| 6404503 | 9/1963 | South Africa . | |
| 1291864 | 10/1972 | United Kingdom . | |
| 1291865 | 10/1972 | United Kingdom . | |

OTHER PUBLICATIONS

Chem. Abstracts 103 (1):6223s (1985).

*Primary Examiner*—Ethel G. Love
*Attorney, Agent, or Firm*—Stuart L. Melton; John J. McDonnell

[57] ABSTRACT

The invention relates to substituted dihydrobenzopyrans carboxylates of the formula:

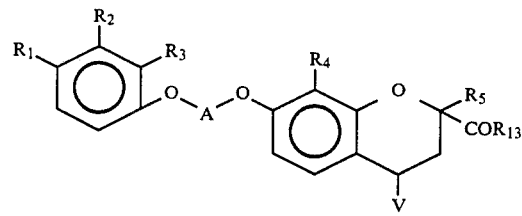

wherein A is a methylene chain having 1–10 carbon atoms, inclusive, optionally substituted by hydroxy;

wherein V is:
(a) hydrogen;
(b) hydroxy;
(c) =O; or
(d) $R_6CH_2O-$;

wherein $R_1$ is:
(a) $-COCH_3$;
(b) $-CHOHCH_3$;
(c) $-C_2H_5$;
(d) -hydrogen; or
(e) $-COOC_2H_5$ wherein $R_2$ is:
(a) -hydrogen;
(b) -hydroxy; or
(c) $R_{12}CH_2CO_2-$;

wherein $R_3$, $R_4$, $R_6$, $R_7$, $R_8$, $R_9$, $R_{10}$, $R_{11}$ and $R_{12}$ each of which may be the same or different, are:
(a) hydrogen;
(b) lower-alkyl having 1–6 carbon atoms inclusive; or
(c) allyl;

wherein $R_5$ is:
(a) hydrogen; or
(b) $R_7CH_2C(O)-$;

wherein $R_{13}$ is hydrogen, hydroxy, alkoxy of 1 to 6 carbon atoms inclusive, or $-OM$ wherein M is an alkali metal, alkyl of 1 to 6 carbon atoms, inclusive, or $NR_8 \oplus R_9R_{10}R_{11}$, or $HNR_8 \oplus R_9R_{10}$, or the pharmacologically acceptable addition salts thereof, which are useful as leukotriene $D_4$ ($LTD_4$) inhibitors and therefore useful in the treatment of allergies and inflammatory conditions.

17 Claims, No Drawings

SUBSTITUTED DIHYDROBENZOPYRAN-2-CARBOXYLATES

BACKGROUND OF THE INVENTION (a) Field of the Invention

This invention in its broadest aspect, relates to inhibitors of metabolic pathways. In particular the invention relates to novel compounds of Formula I which are inhibitors of leukotriene $D_4$ ($LTD_4$) and therefore useful to prevent or alleviate the symptoms or conditions associated with $LTD_4$ such as allergic reactions and inflammatory conditions.

$LTD_4$ is a product of the 5-lipoxygenase pathway and is the major active constituent of slow reacting substance of anaphylaxis (SRS-A) in humans and guinea pigs, Lewis et al. Nature USA, 293: 103-108, (1981). It is a potent bronchoconstrictor that is released during allergic reactions. Because antihistamines are ineffective in the management of asthma it is believed that SRS-A mediates bronchoconstriction resulting from an allergic attack, $LTD_4$ is also a potent inducer of vascular permeability and it also may be involved in other inflammatory conditions such as rheumatoid arthritis, Geller, J., et al., J. Clin. Endocrinol. Metalb. 43: 686-688, (1976).

(b) Information Disclosure

Appleton et al., J. Med. Chem. 20, 371-379 (1977) discloses a series of chromone-2-carboxylic acids which are antagonists of SRS-A. Specifically sodium 7-[3-(4-acetyl-3-hydroxy-2-propylphenoxy)-2-hydroxypropoxy]-4-oxo-8-propyl-4H1-benzopyran-2-carboxylate (FPL 55712), appears to be the first reported specific antagonist of SRS-A and $LTD_4$.

SUMMARY OF THE INVENTION

The invention relates to compounds of the formula:

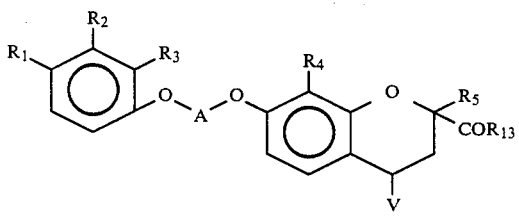

wherein A is a methylene chain having 1-10 carbon atoms, inclusive, optionally substituted by hydroxy;
wherein V is:
 (a) hydrogen;
 (b) hydroxy;
 (c) =O; or
 (d) $R_6CH_2O$—;
wherein $R_1$ is:
 (a) —$COCH_3$;
 (b) —$CHOHCH_3$;
 (c) —$C_2H_5$;
 (d) hydrogen; or
 (e) —$COOC_2H_5$
wherein $R_2$ is:
 (a) hydrogen;
 (b) hydroxy; or
 (c) $R_{12}CH_2CO_2$—;
wherein $R_3$, $R_4$, $R_6$, $R_7$, $R_8$, $R_9$, $R_{10}$, $R_{11}$ and $R_{12}$ each of which may be the same or different, are:
 (a) hydrogen;
 (b) lower-alkyl having 1-6 carbon atoms inclusive; or
 (c) allyl;
wherein $R_5$ is:
 (a) hydrogen; or
 (b) $R_7CH_2C(O)$—;
wherein $R_{13}$ is hydrogen, hydroxy, alkoxy of 1 to 6 carbon atoms inclusive, or —OM wherein M is an alkali metal, alkyl of 1 to 6 carbon atoms, inclusive, or $NR_8{\oplus}R_9R_{10}R_{11}$, or $HNR_8{\oplus}R_9R_{10}$, or the pharmacologically acceptable addition salts thereof, which are useful as leukotriene $D_4$ ($LTD_4$) inhibitors and therefore useful in the treatment of allergies and inflammatory conditions.

Examples of alkyl of 1 to 6 carbon atoms inclusive are methyl, ethyl, propyl, butyl, pentyl, hexyl, and the isomeric forms thereof.

Salts of the acid forms of these compounds can be prepared by neutralization with the appropriate amount of an inorganic or organic base such as sodium hydroxide, potassium hydroxide, calcium hydroxide, magnesium hydroxide, ammonia, trialkylamine, dialkylamine, monoalkylamine, diamino amino acids, triethanolamine and like bases.

$LTD_4$ causes bronchoconstriction when administered to humans and guinea pigs. The bronchoconstriction has 2 components; (a) a direct stimulation of respiratory smooth muscle by $LTD_4$ and (b) an indirect component through release of thromboxane $A_2$ which in turn causes contraction of respiratory smooth muscle. Compounds of the invention antagonize the direct component. The compounds are tested in vivo as follows.

Adult male fasted Hartly guinea pigs weighing 300-350 g are pretreated with pyrilamine and indomethacin to block the bronchoconstricture effects of endogenous histamine and the synthesis of thromboxane $A_2$ respectively. Compounds of the invention are administered IV or IG at appropriate times prior to the IV administration of 2000 units of $LTD_4$.

Intratrachael pressure is monitored prior to and subsequent to $LTD_4$ in animals anesthetized with pentabarbital and attached to a rodent respirator. Compounds which antagonize the direct component of $LTD_4$ action or respiratory smooth muscle inhibit intratrachael insufflation pressure increases (P< or =0.05) caused by $LTD_4$. FPL 55712 is used as a control.

The compounds can be administered in a number of dosage forms. A preferred method of delivery would be oral or in such a manner so as to localize the action of the inhibitor. For example, for asthma, the compounds could be inhaled using an aerosol or other appropriate spray. In an inflammatory condition such as rheumatoid arthritis the compounds could be injected directly into the affected joint. The compounds could also be administered in oral unit dosage forms such as tablets, capsules, pills, powders or granules. They also may be administered rectally or vaginally in such forms as suppositories. They may be introduced in the forms of eyedrops, intraperitoneally, subcutaneously, or intramuscularly using forms known to the pharmaceutical art. For the treatment of inflammatory allergic skin conditions, the compounds of the present invention may also be administered topically in the form of ointments, creams, gels or the like. Regardless of the route of administration selected, the compounds are formulated into pharmaceutically acceptable dosage forms by conventional methods known to the pharmaceutical art.

An effective but non-toxic quantity of the compound is employed in treatment. The dosage regimen for inhibition of LTD₄ by the compounds of this invention is selected in accordance with a variety of factors including the type, age, weight, sex, and medical condition of the mammal, the particular disease and its severity, the route of administration and the particular compound employed. An ordinarily skilled physician or veterinarian will readily determine and prescribe the effective amount of the compound to prevent or arrest the progress of the condition. In so proceeding, the physician or veterinarian could employ or use relatively low dosages at first, subsequently increasing the dose until a maximum response is obtained.

Compounds of this invention may be prepared from chromone intermediates by reduction of the 2,3-double bond. For example, an appropriately substituted phenol I is condensed with a dihaloalkane II to yield a terminally substituted haloalkane III, which is condensed with an appropriately substituted 7-hydroxy chromone IV. The resultant substituted phenoxyalkoxychromone V is reduced to the corresponding chroman-4-one VI, 4-hydroxy chroman VII or chroman VIII, as desired. For example, hydrogen at low pressure in the presence of Raney nickel gives the chroman-4-one, and if the reaction is allowed to continue for a longer period of time, the 4-hydroxy chroman (mixtures can be separated by chromatography). Reduction at higher pressure and temperatures in the presence of palladium or carbon gives the chroman directly. The chroman-4-one can be reduced to the 4-hydroxychroman and/or chroman.

In a modification of approach described in the previous example, an appropriately substituted phenol I is condensed with a haloepoxide IX and the resultant epoxide X condensed with the 7-hydroxy chromone IV to yield compounds XI wherein the alkylene bridge is hydroxy substituted. Compound XI is reduced as discussed in the previous paragraph.

The compounds of the present invention can also be prepared from chroman intermediates. For example, a 7-benzyloxy-2-carboalkoxy chroman XII can be alkylated at the 2-position. The alkylated compound XIII is then debenzylated with hydrogen to give a 7-hydroxy-chroman XIV (benzylation of the 7-hydroxy substituent is required only if the chroman is to be alkylated) which is condensed with a dihaloalkane II. The resultant halo ether XV is condensed with a substituted phenol I to give product XVI.

Other compounds of the invention are made by conventional transformations. For example, esters can be hydrolyzed to corresponding carboxylic acids, carbonyl groups can be reduced with metal hydride reagents, hydroxyl groups acetylated, carboxylic acid ester converted to amides by mixed anhydride procedure, unsaturated side chains reduced to saturated side chains, etc. Such transformations, well known to those skilled in the art, are shown in the Examples which follow.

The invention will appear more fully from the Examples which follow. These Examples are given by way of illustration only and are not to be construed as limiting the invention either in spirit or in scope, as many modifications both in materials and methods will be apparent from this disclosure to those skilled in the art. In these examples, temperatures are given in degrees Celsius (°C.) and quantities of materials in grams and milliliters unless otherwise noted.

EXAMPLE 1

5-(2-n-propyl-3-hydroxy-4-acetylphenoxy)-1-bromopentane

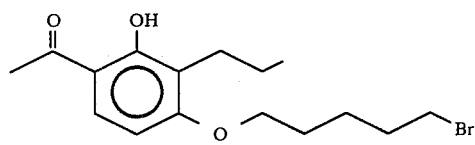

120 g (0.61 mole) of 2,4-dihydroxy-3-n-propylacetophenone, 284 g (1.23 mole) of 1,5-dibromopentane, and 128 g (0.93 mole) anhydrous potassium carbonate were stirred vigorously in 2 l of dry dimethylformamide for 6 hours in a 5 l 3 neck round bottom flask fitted with drying tube, glass stopper, and mechanical stirrer. The suspended solids were removed by filtration and the solvent removed by rotoevaporation at reduced pressure. The brown, oily residue was dissolved in 1 l of 10% ethyl acetate/hexane and insoluble solids were removed by filtration. The filtrate was concentrated by rotoevaporation to a viscous oil that was purified by high pressure liquid chromatography to give 128 g (73%) of the title compound, as a colorless oil. Calc: C, 55.99; H, 6.75; Br, 23.28; Found: C, 55.72; H, 6.85; Br, 23.51.

EXAMPLE 2

2-carboethoxy-7-[5-(2-n-propyl-3-hydroxy-4-acetylphenoxy)pentoxy]-8-n-propylchromone

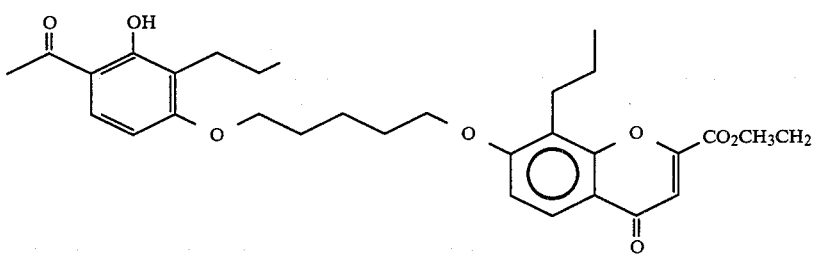

4.67 g (13.6 mmole) of 1-bromo-5-[2-n-propyl-3-hydroxy-4-acetylphenoxy]-pentane, 2.39 g (8.65 mmole) of 2-carboethoxy-7-hydroxy-8-n-propylchromone, and 2.76 g (20 mmole) of anhydrous potassium carbonate were dissolved in 100 ml dimethylformamide in a 250 ml single neck round bottom flask equipped with a magnetic stirring bar and a drying tube charged with calcium chloride. The contents of the flask were stirred at 70° for 18 hours. After cooling, the reaction solution was filtered and the dimethylformamide removed by rotary evaporation. The residual dark red oil was dissolved in 50% ethyl acetate/hexane and purified by chromatography to give 2.07 g (44%) of the title compound, mp 90°–91°. Calc: C, 69.13; H, 7.11; Found: C, 69.44; H, 7.44.

EXAMPLE 3

2-carboethoxy-7-[5-(2-n-propyl-3-hydroxy-4-acetylphenoxy)pentoxy]-8-n-propylchroman-4-one

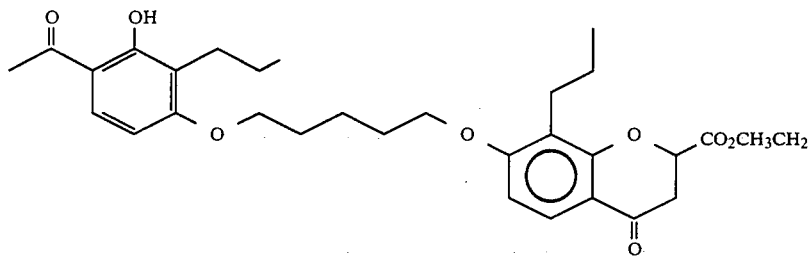

2.45 g (4.55 mmole) of the compound from Example 2 was dissolved in 250 ml of absolute ethanol, 0.5 g $W_2$ Raney nickel added, and the mixture hydrogenated at 2 psi and room temperature for 7 hours. After removal of catalyst by filtration and solvent by rotary evaporation, the residue was purified by high pressure liquid chromatography to furnish 1.26 g (51%) of the title compound, mp 80°–81°. Calc: C, 68.87; H, 7.46. Found: C, 68.70; H. 7.43.

EXAMPLE 4

7-[5-(2-n-propyl-3-hydroxy-4-acetylphenoxy)pentoxy]-8-n-propylchroman-4-one-2-carboxylic acid

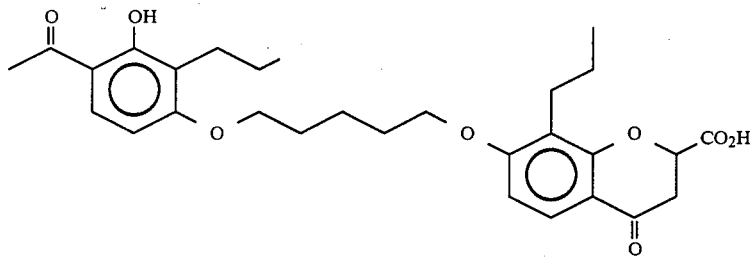

1.35 g (2.5 mmole) of the compound of Example 3 was dissolved in 50 ml of 50% ethanol-tetrahydrofuran in a 250 ml single neck round bottom flask equipped with a magnetic stirring bar. The contents of the flask were cooled to 5° C. in an ice bath and 25 ml of 0.2N sodium hydroxide solution was added. The reaction mixture was stirred at room temperature for eight hours. Most of the solvent was removed by rotoevaporation, 50 ml of water was added and the aqueous mixture acidified with dilute hydrochloric acid. The acidified solution was extracted three times with 150 ml portions of ethyl acetate and the combined extract washed once with brine. The ethyl acetate extract was dried over anhydrous magnesium sulfate, filtered, and the ethyl acetate removed by rotoevaporation to give 1.19 g (93%) of the title compound as a white solid, mp. 166°–168° C. Calc: C, 67.95; H, 7.08, Found: C, 67.79; H, 7.04.

EXAMPLE 5

2-carbomethoxy-7-[5-(2-n-propyl-3-hydroxy-4-acetylphenoxy)pentoxy]-8-n-propylchromone

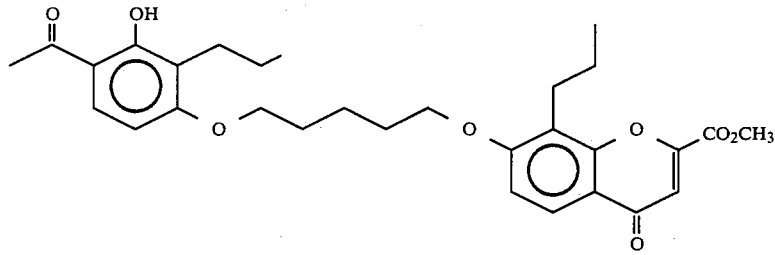

Using the procedure of Example 2, 5.25 g (20 mmoles) of 2-carbomethoxy-7-hydroxy-8-propylchromone and 8.24 g (24 mmoles) of 5-(2-n-propyl-3-hydroxy-4-acetylphenoxy)-1-bromopentane gave 7.0 g (66%) of the title compound, mp 86°–87° C. Calc: C, 68.69; H, 6.92; Found: C, 68.80; H, 6.89.

EXAMPLE 6

2-carbomethoxy-7-[5-(2-n-propyl-3-hydroxy-4-acetyl-phenoxy)pentoxy]-8-n-propylchroman

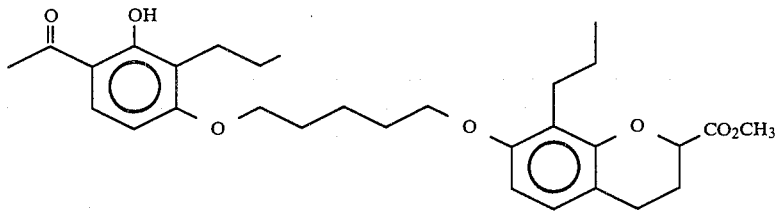

7.65 g (14.6 mmole) of the compound from Example 5 was hydrogenated in 80 ml of acetic acid at 70° C. and 50 psi pressure in a 250 ml Parr shaker using 5% palladium on carbon as the catalyst. Theoretical hydrogen uptake occurred at 40 minutes. The shaker was cooled and vented, and its contents filtered. The filtrate was placed in a rotary evaporator and the acetic acid was removed by azeotropation three times with toluene and then once with methyl alcohol. Recrystallization from ethyl acetatehexane yielded 6.7 g (89%) of the title compound, mp 57°–58°, Calc: C, 70.29; H, 7.86; Found C, 70.09; H, 7.76.

EXAMPLE 7

7-[5-(2-n-propyl-3-hydroxy-4-acetylphenoxy)pentoxy]-8-n-propylchroman-2-carboxylic acid

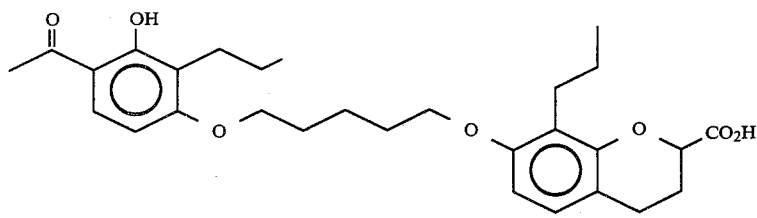

5 g (9.8 mmole) of the methyl ester from Example 6 was placed in a 250 ml round bottom flask and warmed in 100 ml of methyl alcohol to effect dissolution. After cooling to room temperature, 7.5 ml of 2M LiOH was added and the reaction mixture stirred for 3 hours. Solvent was stripped on the rotary evaporator and water added. The solution was acidified to pH 2 with hydrochloric acid, and the resultant gummy mass was extracted with ethyl acetate-ether, washed once with water then with brine, and dried over $Na_2SO_4$. After filtration, the solvent was removed on the rotary evaporator under vacuum at room temperature. Recrystalization form ethyl alcohol gave 3.84 g (79% yield), mp 66°–68° C., of the title compound. Calc: C, 69.86; H, 7.76; Found: C, 70.05; H, 7.68.

EXAMPLE 8

2-carbomethoxy-7-[5-(2-n-propyl-3-hydroxy-4-ethyl-phenoxy)pentoxy]-8-n-propylchroman

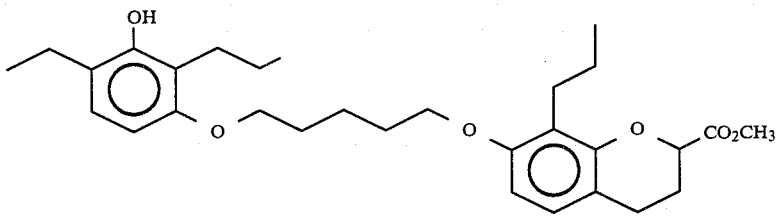

5.25 (10 mmole) of the compound from Example 5, was dissolved in 125 ml of glacial acetic acid and 0.5 g of 5% palladium on carbon added. The resulting suspension was hydrogenated at 70° C. and 50 psi for two hours. The reaction mixture was cooled and filtered to remove catalyst. After removing the solvent by rotary evaporation, the residue was purified by high pressure liquid chromatography to furnish 1.76 g (35%) of the title compound as an oil. Calc: C, 72.26; H, 8.49; Found: C, 72.20; H, 8.59.

EXAMPLE 9

7-[5-(2-n-propyl-3-hydroxy-4-ethylphenoxy)pentoxy]-8-n-propylchroman-2-carboxylic acid

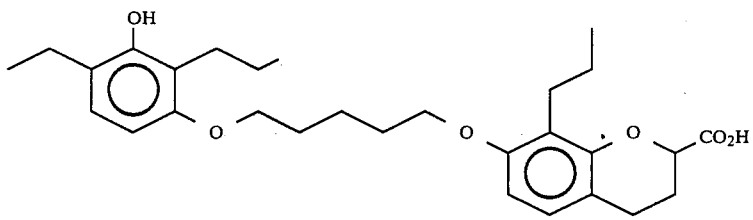

1.26 g (2.5 mmole) of the methyl ester from Example 8 was dissolved in 25 ml of methanol in a single neck 100 ml round bottom flask. Next a solution of 202 mg (5 mmole) of sodium hydroxide in 10 ml water was added. The resulting mixture was stirred with the aid of a magnetic stirring bar for 2 hours at room temperature. The methanol was removed by rotary evaporation and the residue was acidified with dilute hydrochloric acid to pH 2. The acidified solution was extracted three times with 30 ml portions of ethyl acetate. The combined ethyl acetate extracts were dried over anhydrous magnesium sulfate, filtered and the ethyl acetate removed by rotoevaporation to furnish 1.16 g (95%) of the title compound, mp 101°–102°. Calc: C, 71.87; H, 8.32; Found: C, 71.71; H, 8.31.

EXAMPLE 10

5-(2-allyl-4-carbomethoxyphenoxy)-1-bromopentane

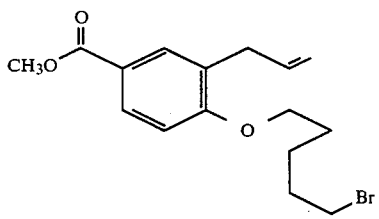

Using the procedure of Example 1, 5.62 g (29.2 mmole) of methyl 3-allyl-4-hydroxybenzoate and 13.8 g (60 mmole) of 1,5-dibromopentane gave 6.9 g (69%) of the title compound as an oil. Calc: C, 56.32; H, 6.20; Found; C, 55.91; H, 6.20.

EXAMPLE 11

2-carbomethoxy-7-[5-(2-allyl-4-carbomethoxyphenoxy)pentoxy]-8-n-propylchromone

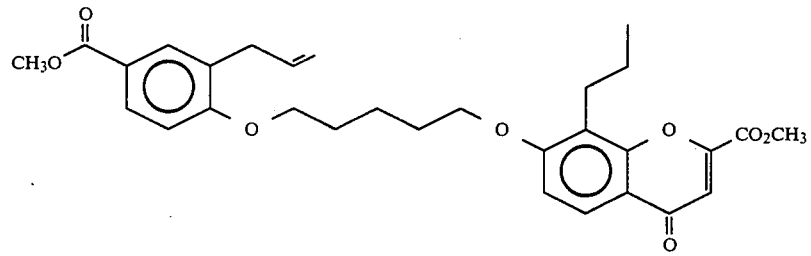

Using the procedure of Example 2, 4.14 g (15.8 mmole) of methyl 7-hydroxy-8-n-propylchromone-2-carboxylate and 5.63 g (16.5 mmole) of the compound from Example 10 gave 7.9 g (96%) of the title compound, mp 87°–88°. Calc: C, 68.95; H, 6.61; Found; C, 68.49; H, 6.54.

EXAMPLE 12

2-carbomethoxy-7-[5-(2-n-propyl-4-carbomethoxyphenoxy)pentoxy]-8-n-propylchroman

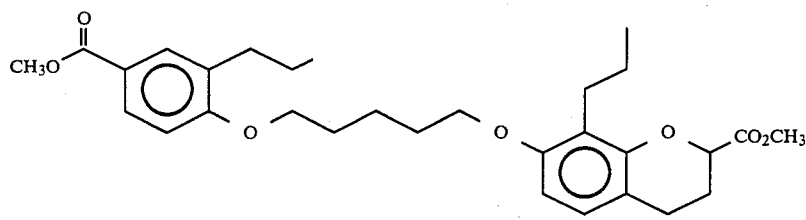

5.38 (10.3 mmole) of the compound from Example 11 was dissolved in 170 ml of 30% tetrahydrofuran-methanol and 538 mg of 5% palladium on carbon added. The resulting suspension was hydrogenated at 2 psi and room temperature for 2 hours. After separation of catalyst by filtration, the solvent was removed by rotary evaporation. The solid residue was washed with a small amount of methanol and filtered to give 3.86 g (71%) of allyl-group reduced compound, mp 79°–80°. Calc: C, 68.69; H 6.92; Found; C, 68.41; H, 6.94.

2.62 g (5 mmole) of that compound was dissolved in 30 ml glacial acetic acid, 262 mg of 5% palladium on carbon added, and the suspension hydrogenated at 50 psi and 70° for 160 minutes. After filtration to separate the catalyst, the acetic acid was removed by rotary evaporation to give 2.12 g (83%) of the title compound, mp 63°–64°. Calc: C, 70.29; H, 7.86; Found; C, 69.91; H, 7.84.

EXAMPLE 13

7-[5-(2-n-propyl-4-carbomethoxyphenoxy)pentoxy]-8-n-propylchroman-2-carboxylic acid

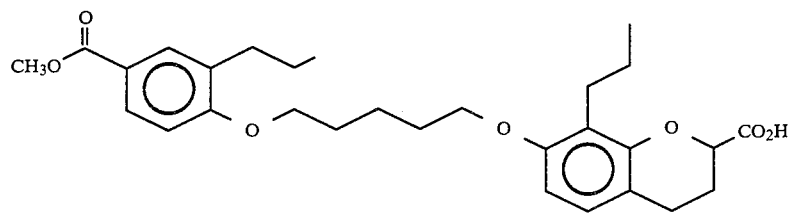

Using the procedure of Example 9, 1.79 g (3.5 mmole) of the compound of Example 12 gave 1.63 g (94%) of the half-ester title compound, mp 77°–78° C. Calc: C, 69.40; H, 7.49; Found, C, 69.54; H, 7.71.

EXAMPLE 14

3-(2-n-propyl-3-hydroxy-4-acetylphenoxy)-1-bromopropane

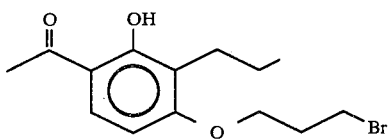

Using the procedure essentially of Example 1 and methyl ethyl ketone as the solvent, 50 g (0.257 mole) of 2,4-dihydroxy-3-n-propylacetophenone and 52 ml (0.51 mole) of 1,3-dibromopropane gave 54 g (67%) of the title compound as a low melting solid, mp 38°–40°. Calc: C, 53.35; H, 6.08; Found; C, 53.11, H, 5.95.

EXAMPLE 15

2-carbomethoxy-7-[3-(2-n-propyl-3-hydroxy-4-acetylphenoxy)propoxy]-8-n-propylchromone.

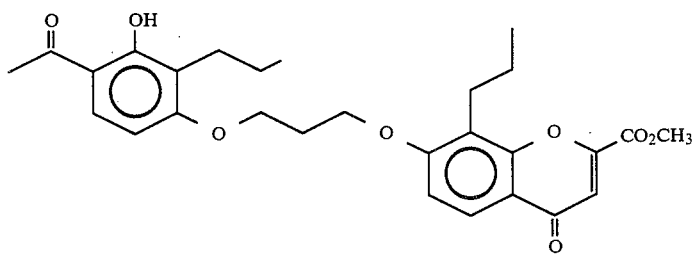

Using the procedure of Example 2, 5.25 g (120 mmole) of methyl 7-hydroxy-8-n-propylchromone-2-carboxylate and 6.93 g (22 mmole) of the compound of Example 14 gave 7.54 g (76%) of the title compound, mp. 113°–115°. Calc: C, 67.73; H, 6.50; Found: C, 67.71; H, 6.49.

EXAMPLE 16

2-carbomethoxy-7-[3-(2-n-propyl-3-hydroxy-4-acetylphenoxy)propoxy]-8-n-propylchroman.

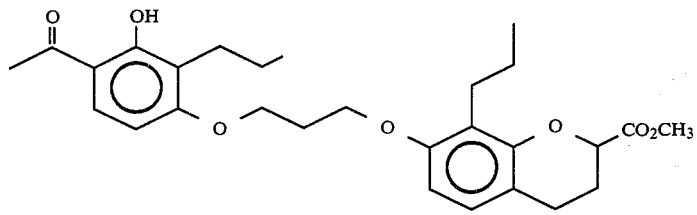

7.06 g (14.2 mmole) of the compound from Example 15 was hydrogenated to give 5.46 g (79%) of the title compound, mp 70°–72°. Calc: C, 68.92; H, 7.28; Found; C, 68.72; H, 7.38.

EXAMPLE 17

7-[3-(2-n-propyl-3-hydroxy-4-acetylphenoxy)propoxy]-8-n-propylchroman-2-carboxylic acid.

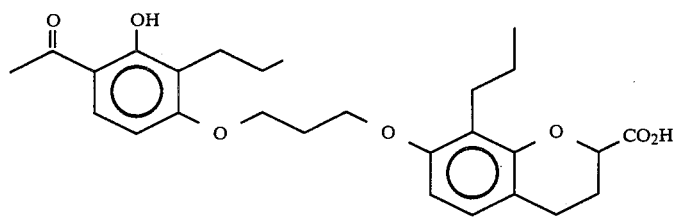

3.17 g (6.54 mmole) of the compound from Example 16 was saponified using the method of Example 7 to give 2.84 g (92%) of the title compound, mp 108°–109°. Calc: C, 68.92; H, 7.28; Found: C, 68.82; H, 7.27.

EXAMPLE 18

3-(2-n-propyl-3-hydroxy-4-acetylphenoxy)-1,2-epoxypropane

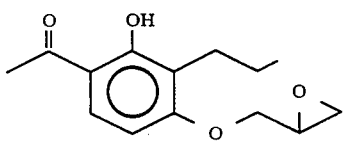

2,4-dihydroxy-3-n-propylacetophenone, 9.7 g (50 mmole), and 11.8 ml (150 mmole) of epichlorohydrin were dissolved in 20 ml of refluxing ethanol. A solution of 3.1 g (55 mmole) potassium hydroxide in 20 ml ethanol and containing 0.4 ml water was added dropwise to the refluxing ethanol. After the addition was complete, the reaction mixture was refluxed for an additional three hours. 100 ml water was added to the cooled reaction mixture and the product extracted with ether. After decolorization with charcoal, drying over anhydrous magnesium sulfate, and evaporation of the ether, the residual oil was distilled, b.p. 165°/0.7 mm, to furnish 8.3 g (55%) of product. The distillate was triturated with hexane and filtered to furnish crystalline title compound, mp. 53°–55° C. Calc: C, 67.18; H, 7.25. Found; C, 66.72; H, 7.38.

EXAMPLE 19

2-carbomethoxy-7-[3-(2-n-propyl-3-hydroxy-4-acetylphenoxy)-2-hydroxypropoxy]-8-n-propylchromanone

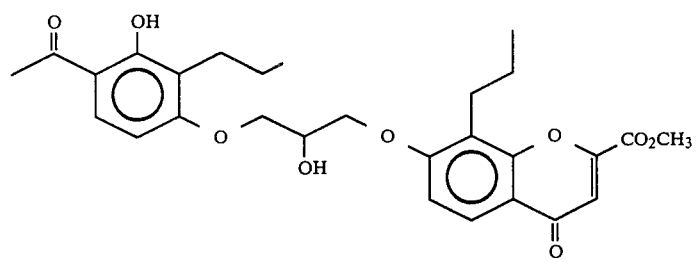

A 250 ml single neck round bottom flask was charged with 3.75 g (15 mmole) of the product of Example 18, 3.93 g (15 mmole) of methyl 7-hydroxy-8-n-propylchromone-2-carboxylate, 100 ml of dimethylformamide, and 4 drops of Triton B. The flask was equipped with a magnetic stirring bar and a calcium chloride drying tube and was heated at 100° C. for 48 hours. The dimethylformamide was removed by rotary evaporation and the resulting residue dissolved in ethyl acetate and filtered. The ethyl acetate was evaporated and the residue purified by high pressure liquid chromatography (50% ethyl acetate-hexane) twice to give 853 mg (11%) of crystalline title compound: Calc: C, 65.61; H, 6.29; Found; C, 65.47; H, 6.39.

EXAMPLE 20

7-[3-(2-n-propyl-3-hydroxy-4-acetylphenoxy)-2-hydroxypropoxy]-8-n-propylchroman-2-carboxylic acid

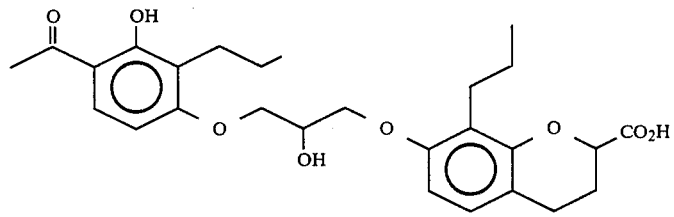

The compound of Example 19, 853 mg (1.66 mmole) was hydrogenated essentially according to the procedure of Example 6. The ester was saponified essentially according to the procedure of Example 7 to give 280 mg (93%) of vanilla colored title compound, mp 127°–28°. Calc: C, 66.65; 4, 7.04; Found; C, 66.49; H, 7.06.

EXAMPLE 21

Methyl 7-hydroxy-8-n-propylchroman-2-carboxylate

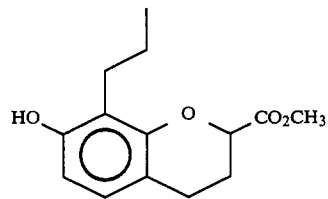

6.56 g (25 mmole) of methyl 7-hydroxy-8-n-propylchromone-2-carboxylate was dissolved in 125 ml of acetic acid and 656 mg of 5% palladium on carbon added. The resulting suspension was hydrogenated at 50 psi and 70° C. for 4 hours. After cooling, the catalyst was separated by filtration and the acetic acid removed by rotary evaporation. The residue was purified by high pressure liquid chromatography (15% ethyl acetate-hexane) to give 5.25 g (84%) of the methyl ester, mp 51°–53°. Calc: C, 67.18; H, 7.25; Found; C, 67.10; H. 7.41.

EXAMPLE 22

Methyl 7-benzyloxy-8-n-propylchroman-2-carboxylate

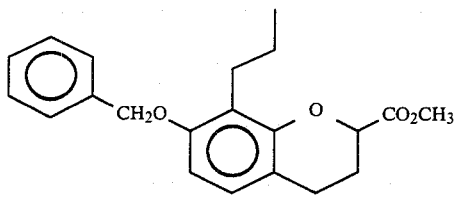

A 250 ml single neck round bottom flask was charged with 5.25 g (21 mmole) of methyl 7-hydroxy-8-n-propylchroman-2-carboxylate, 150 ml of dimethylformamide, 3.59 g (26 mmole) of anhydrous potassium carbonate, and 4.30 g (25 mmole) of benzyl bromide. The flask was stoppered and stirred (magnetic stirrer) at room temperature for 4 hours. The insoluble solids were separated by filtration and the dimethylformamide removed by rotary evaporation. The residue was dissolved in 200 ml ethyl acetate, clarified by filtration, and concentrated to an oily residue by rotary evaporation. The resultant crude material was purified by high pressure liquid chromatography (5% ethyl acetate-hexane), to obtain 5.48 g (77%) of the title compound as a clear oil. Calc: C, 74.09; H, 7.11; Found; C, 74.11; H, 7.06.

EXAMPLE 23

Methyl 2-methyl-7-benzyloxy-8-n-propylchroman-2-carboxylate

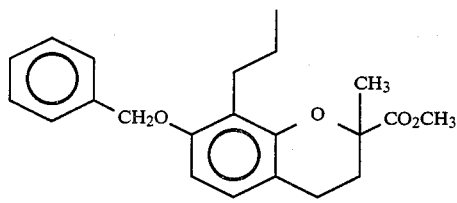

A 3 neck 100 ml round bottom flask equipped with a magnetic stirring bar, dropping funnel, glass stopper, and gas inlet tube was purged with argon and flame dried. Dry tetrahydrofuran (35 ml) and 1.08 ml (7.7 mmole) of diisopropylamine was introduced, the flask cooled to 0° C. and 3.6 ml of 2.14 n-butyl lithium in hexane (7.7 mmole) introduced via syringe. After stirring 10 minutes at 0° C., the flask was cooled to −70° C. and a solution of 2.38 g (7 mmole) of methyl ester in 25 ml of dry tetrahydrofuran was added dropwise; the reaction mixture was stirred for an additional hour at −70°. 1.093 g (7.7 mmole) of methyl iodide in 10 ml of dry tetrahydrofuran was added dropwise to the reaction mixture still at −70°. After the addition was complete, the reaction mixture was allowed to warm slowly to room temperature. Most of the solvent was removed by rotary evaporation, 50 ml water added, the residue acidified with 10% hydrochloric acid. The acidified solution was extracted twice with 50 ml portions of ethyl acetate, the ethyl acetate extracts washed once with saturated sodium bicarbonate, once with brine, and dried with anhydrous magnesium sulfate, filtered and concentrated by rotary evaporation to furnish 2.15 g of crude product. Purification by high pressure liquid chromatography (5% ethyl acetate-hexane) gave 1.81 g (73%) of the title compound as a colorless oil. Calc: C, 74.55; H, 7.39; Found; C, 74.31; H, 7.30.

EXAMPLE 24

Methyl 2-methyl-7-hydroxy-8-n-propylchroman-2-carboxylate

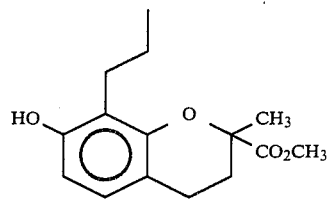

The compound of Example 23, 1.76 g (5 mmole) was dissolved in 30 ml methanol and 176 mg of 5% palladium on carbon was added. The resulting suspension was hydrogenated at 60 psi at 60° C. for one hour. After removal of the catalyst by filtration and solvent by rotary evaporation, 1.3 g (99%) of phenolic methyl ester was obtained. The phenol was homogenous by thin layer chromatography (10% ethyl acetate-hexane).

EXAMPLE 25

Methyl 2-methyl-7-(3-bromopropoxy)-8-n-propylchroman-2-carboxylate

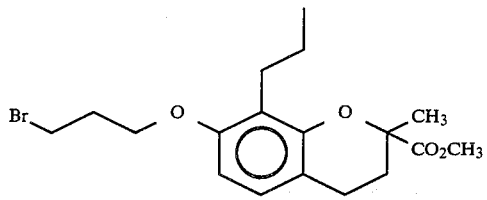

A 100 ml single neck round bottom flask was charged with 1.30 g (4.9 mmole) of the compound of Example 24, 11.51 g (57 mmole) of 1,3-dibromopropane, 1.05 g (7.6 mmole) of anhydrous potassium carbonate, and 15 ml of methyl ethyl ketone. The flask was fitted with a magnetic stirring bar and condenser topped with a calcium chloride drying tube and the solution refluxed with stirring for 48 hours. Methylene chloride, 50 ml was added to the flask and insoluble solids were removed by filtration. The volatile solvents were then removed by rotary evaporation and the excess dibromopropane removed at reduced pressure. The crude bromoester was purified by high pressure liquid chromatography (10% ethyl acetate-hexane) to give 1.5 g (79%) of the title compound as a colorless oil. Calc: C, 56.11; H, 6.54, Br, 20.74; Found; C, 56.62, H, 6.52; Br, 20.25.

EXAMPLE 26

2-carbomethoxy-2-methyl-7-[3-(2-n-propyl-3-hydroxy-4-acetylphenoxy)propoxy]-8-n-propylchroman.

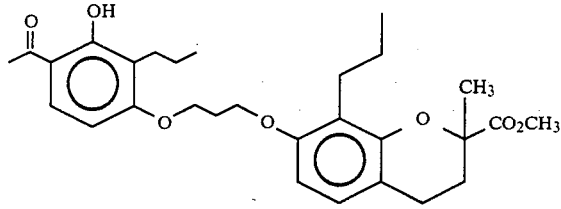

A single neck 50 ml round bottom flask equipped with drying tube and magnetic stirring bar was charged with 1.46 g (3.8 mmole) of the compound from Example 25, 7.38 mg (3.8 mmole) of 2,4-dihydroxy-3-n-propylacetophenone, 1.05 g (7.6 mmole) of anhydrous potassium carbonate and 25 ml of dimethylformamide, and the contents stirred for 18 hours at room temperature. The solution was filtered to remove inorganic solids and the dimethylformamide filtrate removed by rotary evaporation. The resulting residue was dissolved in 50 ml of ethyl acetate and clarified by filtration. After removal of ethyl acetate by rotary evaporation, the crude product was purified by high pressure liquid chromatography (18% ethyl acetate-hexane) to give 1.28 g (68%) of the title compound as an oil. Calc: C, 69.85; H, 7.68; found; C, 69.69; H 7.75.

EXAMPLE 27

2-methyl-7-[3-(2-n-propyl-3-hydroxy-4-acetylphenoxy)propoxy]-8-n-propylchroman-2-carboxylic acid

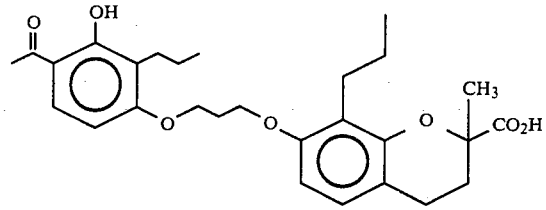

Using the procedure of Example 7 the methyl ester of Example 26, 1.01 g (2.0 mmole), was saponified to give 680 mg (70%) of the title acid, mp 110°-112°. Calc: C, 69.40; H, 7.49; Found; C, 68.84; H, 7.45.

EXAMPLE 28

2-carboethoxy-7-[5-(2-n-propyl-3-hydroxy-4-acetylphenoxy)pentoxy]-4-hydroxy-8-n-propylchroman

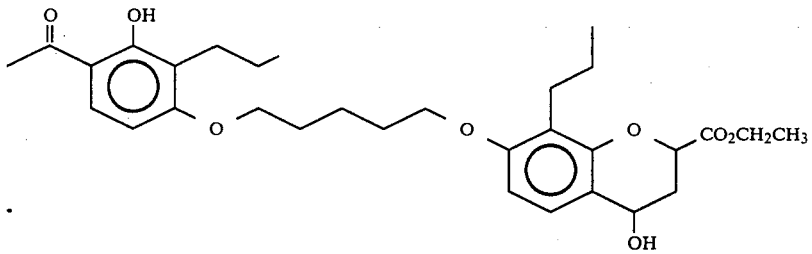

The compound of Example 2, 14.3 g (0.027 mole), was dissolved in 150 ml tetrahydrofuran and 150 ml ethyl alcohol and hydrogenated using Raney Nickel (4.2 g) at 2 psi. After 24 hours at room temperature, the catalyst was separated by filtration and the solvent stripped to give crude (14.4 g oil). 2.4 of the crude was chromatographed (50% ethyl acetate-hexane) to give 1.4 g (50% yield based on crude taken) of the title compound as an oil. Calc: C, 68.61; H, 7.80. Found: C, 68.34; H, 7.74.

EXAMPLE 29

7-[5-(2-n-propyl-3-hydroxy-4-acetylphenoxy)pentoxy]-4-hydroxy-8-n-propylchroman-2-carboxylic acid

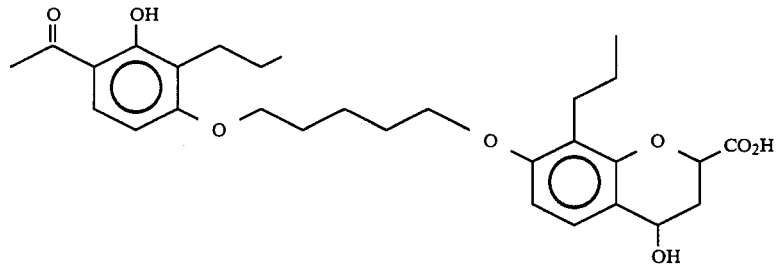

1.2 g (2.2 mmole) of the compound of Example 28 dissolved in 20 ml ethanol and 35 ml tetrahydrofuran was saponified with 0.3 g NaOH, the reaction mixture acidified with dilute HCl to pH 3 and extracted with ethyl acetate. The organic phase was washed with water until neutral, then with brine and dried with magnesium sulfate. The crude residue after evaporation of the solvent was triturated with benzene and 0.18 (16%) of the title compound as a white solid, mp 95.5°–97.5° C., separated by filtration. Calc: C, 67.68; H, 7.44; Found: C, 67.56; H, 7.34.

EXAMPLE 30

2-carboethoxy-7-[5-(2-n-propylphenoxy)pentoxy]-8-n-propylchromone

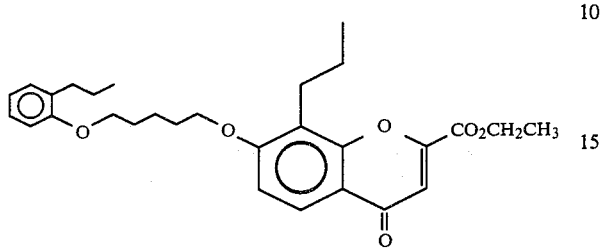

Using essentially the method of Example 2, 2.76 g (10 mmole) of ethyl 7-hydroxy-8-n-propylchromone-2-carboxylate and 8.18 g (11 mmole) of 5-(2-n-propylphenoxy)-1-bromopentane, gave 3.84 g (80%) of the title compound, mp 73°–75°. Calc: C, 72.48; H, 7.55; Found: C, 72.24; H, 7.63.

EXAMPLE 31

2-carboethoxy-7-[5-(2-n-propylphenoxy)pentoxy]-8-n-propylchroman-4-one

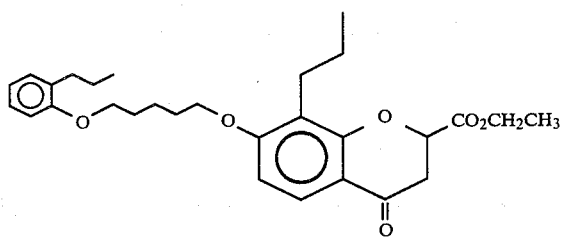

961 mg (2 mmole) of the compound of Example 30 was dissolved in 30 ml of 50% tetrahydrofuran-ethanol and 96 mg of Raney Nickel was added. The resulting suspension was hydrogenated at 2 psi and room temperature for 30 minutes. After separation of the catalyst by filtration, the solvent was removed by rotary evaporation to yield 855 mg (89%) of the title compound as a clear oil. Calc: C, 72.17; H, 7.94; Found: C, 71.84; H. 8.00.

EXAMPLE 32

7-[5-(2-n-propylphenoxy)pentoxy]-8-n-propylchroman-4-one-2-carboxylic acid

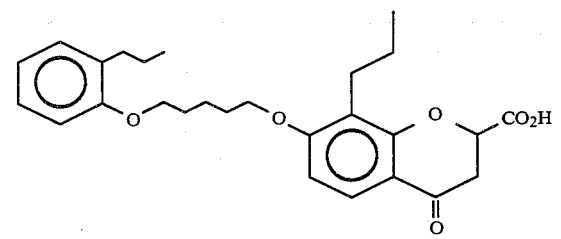

The compound of Example 31, was saponified using essentially the procedure of Example 29, to give 360 mg (57%) of the title compound as a vanilla solid mp 128°–130°. Calc: C, 71.34; H, 7.54; Found; C, 71.43; H, 7.65.

EXAMPLE 33

2-hydroxymethyl-7-benzyloxy-8-n-propylchroman

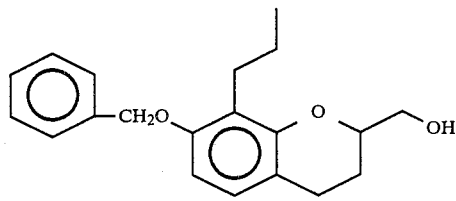

A 3 neck 250 ml round bottom flask fitted with a magnetic stirring bar, a dropping funnel, a gas inlet tube, and a glass stopper was flame dried and flushed with argon. 100 ml of dry ether was introduced and 331 mg (15.2 mmole) of lithium borohydride was added to the ether. A solution of 5.17 g (15.2 mmole) of the compound of Example 32 in 50 ml of ether was added dropwise to the stirred slurry of borohydride. After the addition was completed, the solution was stirred for 2 hours additional at room temperature. The flask was cooled in an ice bath and 20 ml of water added dropwise followed by the careful dropwise addition of dilute hydrochloric acid until the solution cleared. The aqueous layer was drained off in a separatory funnel and the ether washed once with saturated sodium bicarbonate solution and then with brine. Drying the ether with anhydrous magnesium sulfate, filtration to separate the drying agent and ether removal by rotary evaporation gave 4.34 g (91%) of the title compound as an oil. Calc: C, 76.89; H, 7.74; Found: C, 76.75; H, 7.66.

EXAMPLE 34

2-hydroxymethyl-7-hydroxy-8-n-propylchroman

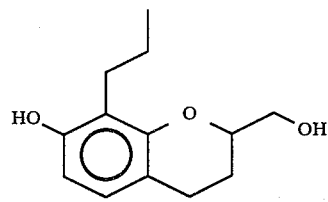

3.97 g (12.7 mmole) of the compound from Example 33 was dissolved in 30 ml of methanol and 397 mg of 5% palladium on carbon was added. The resulting suspension was hydrogenated at 60 psi and 60° C. for 46 minutes. After cooling and removal of the catalyst by filtration, the solvent was removed by rotary evaporation to give 2.80 g (99%) of the title compound as a light yellow oil. Calc: C, 70.25; H, 8.16; Found: C, 69.54; H 8.18.

EXAMPLE 35

2-hydroxymethyl-7-(5-bromopentoxy)-8-n-propylchroman

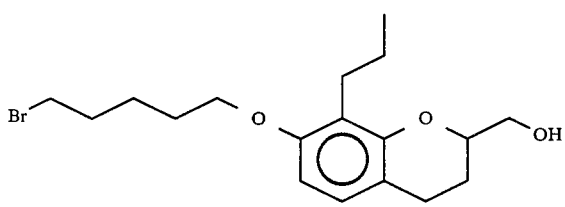

A 250 ml single neck round bottom flask was charged with 2.70 g (12.15 mmole) of the compound from Example 34, 42 g or 25 ml (182 mmole) of 1,5-dibromopentane, 2.07 g (15 mmole) of anhydrous potassium carbonate, 750 mg (5 mmole) of sodium iodide, and 150 ml of methyl ethyl ketone. The flask was fitted with a magnetic stirring bar and a condenser topped with a calcium chloride drying tube and the reaction was refluxed for 5 days. The undissolved solids were removed by filtration and the filtrate was concentrated in vacuo on a rotary evaporator. The crude liquid residue was purified by high pressure liquid chromatography (20% ethyl acetate-hexane) to give 2.69 g (82%) of the title compound as a light yellow oil. Calc: C, 58.22; H, 7.33; Found: C, 58.10; H, 7.24.

EXAMPLE 36

2-hydroxymethyl-7-[5-(2-n-propyl-3-hydroxy-4-acetylphenoxy)pentoxy]-8p-n-propylchroman

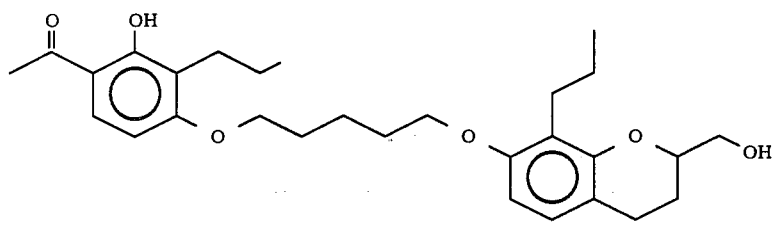

3.38 g (9.1 mmole) of the bromopentane from Example 35, 1.77 g (9.1 mmole) of 2,4-dihydroxy-3-n-propylacetophenone, and 2.07 g (15 mmole) of anhydrous potassium carbonate were dissolved in 25 ml dry dimethylformamide contained in a 50 ml single neck round bottom flask fitted with a magnetic stirring bar and a calcium chloride drying tube. The contents of the flask were stirred at room temperature for 18 hours. The insoluble solids were removed by filtration and the solvent removed by rotary evaporation. The residue was dissolved in 75 ml of ethyl acetate and insoluble solids removed by filtration. The ethyl acetate was removed by rotary evaporation and the residue purified by high pressure liquid chromatography (25% ethyl acetate-hexane) to furnish 3.11 g (71%) of the title compound as a light yellow oil that crystallized, mp 58°–59°. Calc: C, 71.87; H, 8.32; Found: C, 71.52; H, 8.31.

EXAMPLE 37

2-formyl-7-[5-(2-n-propyl-3-hydroxy-4-acetylphenoxy)pentoxy]-8-n-propylchroman.

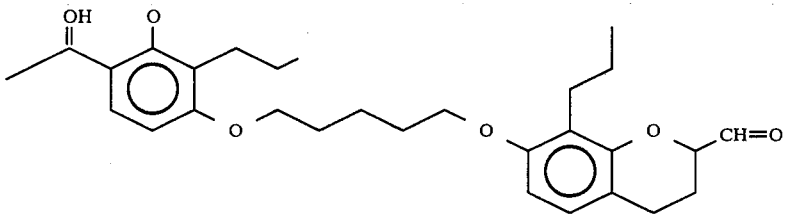

A 3 neck 50 ml round bottom flask fitted with a magnetic stirring bar, gas inlet tube, low temperature thermometer and dropping funnel was flushed with argon and flame dried. 10 ml of methylene chloride was followed by 444 mg (3.5 mmole) of oxalyl chloride. After cooling to −60° C., dimethylsulfoxide 0.51 ml 0.52 g (6.65 mmole) was added dropwise and the solution stirred 10 minutes. A solution of 1.48 g (3.05 mmole) of the compound of Example 36 in 5 ml methylene chloride was added dropwise maintaining the reaction at −60° C. After the addition was complete, the reaction mixture was stirred for 15 minutes additional at −60° C. 2.13 ml or 1.543 g (15.25. mmole) of triethylamine at −60° C. was added and the reaction mixture allowed to warm to room temperature. 10 ml of water was added and the organic layer separated and washed with 1% hydrochloric acid, sodium bicarbonate solution, water, dried with anhydrous magnesium sulfate, filtered, and the solvent removed by rotary evaporation. The crude oil was purified by high pressure liquid chromatography (25% ethyl acetate-hexane) to give 620 mg (42%) of the title compound as an oil: Calc: C, 72.17; H 7.94; Found: C, 71.84; H, 8.02

EXAMPLE 38

Methyl 2-acetyl-7-benzyloxy-8-n-propylchroman-2-carboxylate

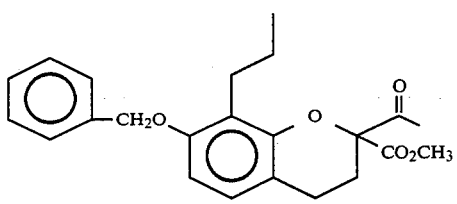

A 100 ml 3 neck roundbottom flask was fitted with a magnetic stirring bar, dropping funnel, serum cap, and gas inlet tube, flushed with argon and flame dried. 1.11 g or 1.54 ml (11 mmole) of diisopropylamine and 30 ml dry tetrahydrofuran were added. After cooling to −20° C., 6.43 ml of 1.71M n-butyl lithium (11 mmole) was added dropwise via syringe. The solution was stirred 15 minutes at −10° C. and then cooled to −70° C. 3.40 g (10 mmole) of the product of Example 22 in 20 ml tetrahydrofuran at −70° C. was added dropwise over a period of half hour. After stirring one additional hour at −70° C., 1.27 g (11.5 mmole) of acetylimidazole in 10 ml tetrahydrofuran was added and the reaction mixture allowed to warm slowly to −10° C. 0.5M potassium hydrogen sulfate solution was added until the pH reached 2.0, the layers were separated and 100 ml ethyl acetate was added. The organic layer was washed with 0.5M potassium hydrogen carbonate, twice with water and then dried with anhydrous magnesium sulfate. After filtration, the ethyl acetate was removed by rotary evaporation and the residual oil purified by high pressure liquid chromatography (10% ethyl acetate-hexane) to give 2.42 g (63%) of the title compound as an oil. Calc: C, 72.22; H, 6.85; Found: C, 72.43; H, 6.86.

EXAMPLE 39

Methyl 2-acetyl-7-hydroxy-8-n-propylchroman-2-carboxylate

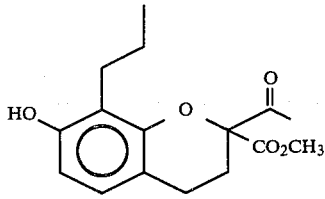

920 mg (2.41 mmole) of the compound from Example 38 was dissolved in 50 ml methanol and 92 mg 5% palladium on carbon added. The suspension was hydrogenated at room temperature and 2 psi for 2.5 hours. Removal of the catalyst by filtration and removal of methanol by rotary evaporation gave 640 mg (91%) of the title compound as a light orange oil, which began to crystallize on standing, homogeneous by thin layer chromatography in 20% ethyl acetate-hexane.

EXAMPLE 40

Methyl 2-acetyl-7-(3-bromopropoxy)-8-n-propylchroman-2-carboxylate

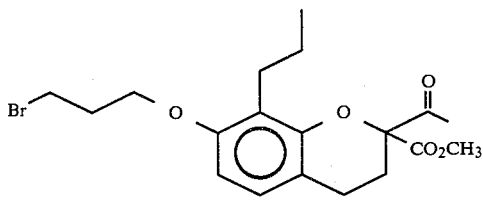

A 50 ml single neck round bottom flask was charged with 640 mg (2.2 mmole) of the compound from Example 39, 6.63 g or 3.33 ml (32.8 mmole) of 1,3-dibromopropane, 690 mg (5 mmole) of anhydrous potassium carbonate, 150 mg (1 mmole) of sodium iodide, and 4 ml of methyl ethyl ketone. The flask was equipped with a magnetic stirring bar and a condenser topped with a calcium chloride drying tube, and refluxed with stirring for 72 hours. The insoluble solids were removed by filtration and the filtrate was concentrated by rotary evaporation. Purification of the residual oil by high pressure liquid chromatography (15% ethyl acetate-hexane) gave 400 mg (44%) of the title compound as a clear oil, homogenous by this layer chromatrography (20% ethyl acetate-hexane).

EXAMPLE 41

Methyl 2-acetyl-7-[3-(2-n-propyl-3-hydroxy-4-acetylphenoxy)-propoxy]-8-n-propylchroman-2-carboxylate

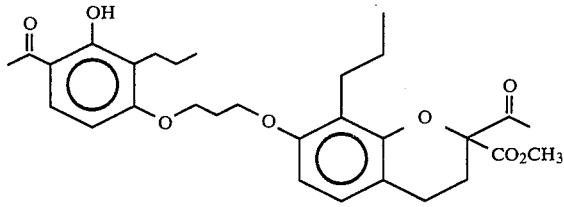

400 ml (0.97 mmole) of the compound from Example 40, 241 mg (1.1 mmole) of 2,4-dihydroxy-3-n-propylacetophenone, 304 mg (2.2 mmole) of anhydrous potassium carbonate, and 20 ml of dimethylformamide were added to a 50 ml single neck round bottom flask. The flask, equipped with a magnetic stirring bar and a calcium chloride drying tube, was stirred 18 hours at room temperature. The insoluble material was removed by filtration and the solvent was removed by rotary evaporation. The residue was then dissolved in ethyl acetate, clarified by filtration, and the ethyl acetate removed by rotary evaporation. The residue was purified by high pressure liquid chromatography (20% ethyl acetate-hexane) to give 240 mg (47%) of the title compound as a clear oil that crystallized on standing, mp 58°–59° C. Calc: C, 68.42; H, 7.27; Found: C, 68.29; H, 7.37.

EXAMPLE 42

2-acetyl-7-[3-(2-n-propyl-3-hydroxy-4-acetylphenoxy)-propoxy]-8-n-propylchroman.

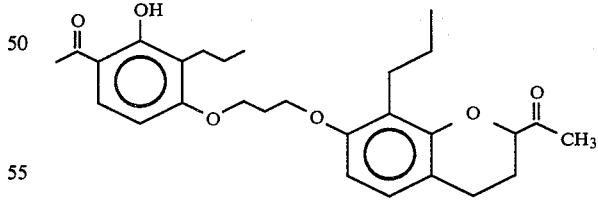

240 mg (0.46 mmole) of the compound from Example 41 was dissolved in 5 ml methanol and 0.5 ml of 2M lithium hydroxide (1.0 mmole) was added; the solution turned yellow and solidified on standing 3 hours. The reaction mixture was warmed on a steam bath and allowed to stand overnight at room temperature. Methanol was removed by rotary evaporation and the residue dissolved in ethyl acetate. The ethyl acetate solution was washed with 5% hydrochloric acid, saturated sodium bicarbonate, and water, and dried with anhydrous magnesium sulfate. After filtration to remove magnesium sulfate, the solvent was removed by rotary evaporation. The crude product was purified by passage through silica gel with 50% ethyl acetate-hexane to yield 40 mg (20%) crystalline solid, mp 60°–61°, as its half-hydrate. Calc: C, 70.41, H, 7.81; Found: C, 70.60; H, 7.38.
CHART A
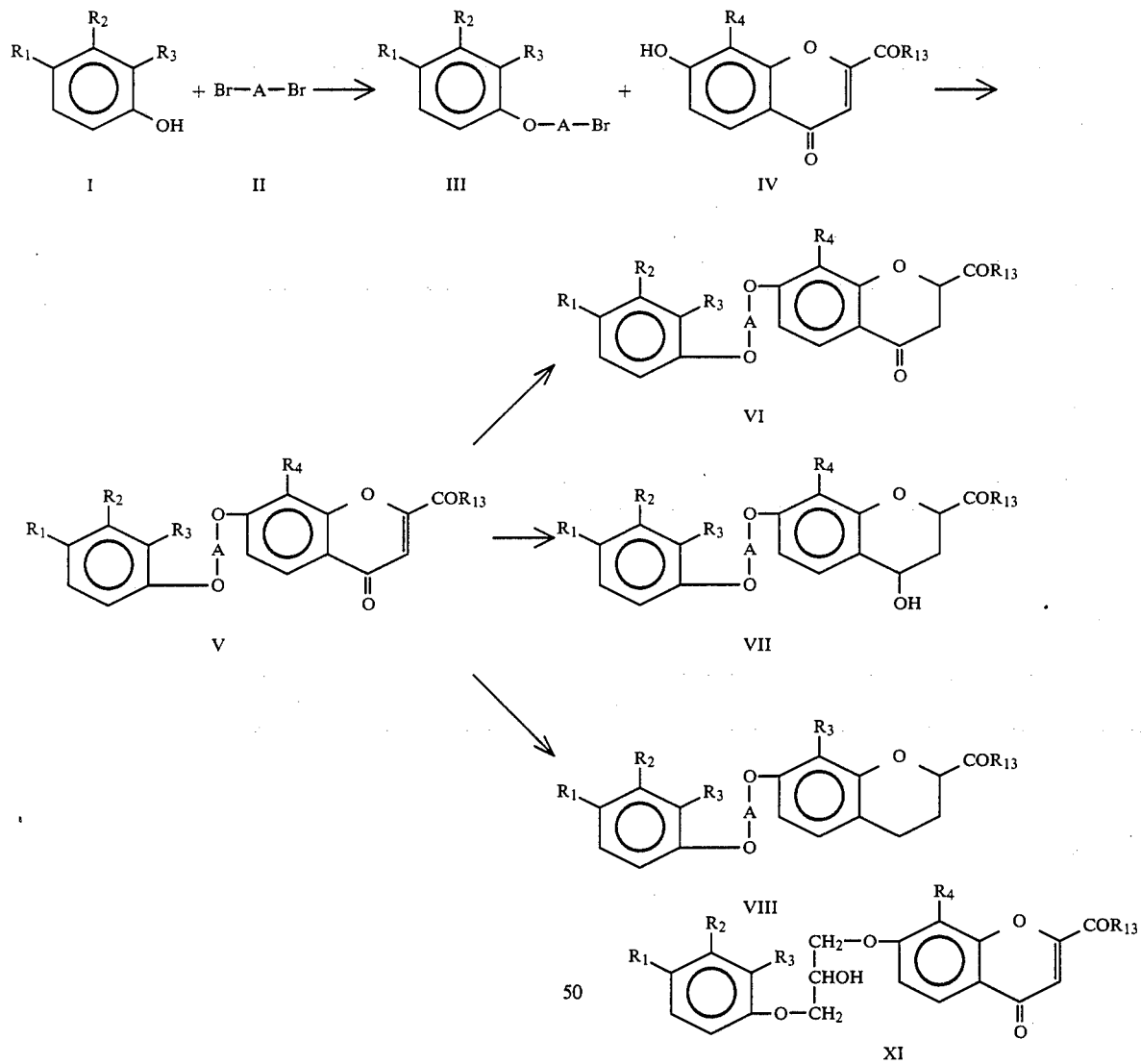
CHART B
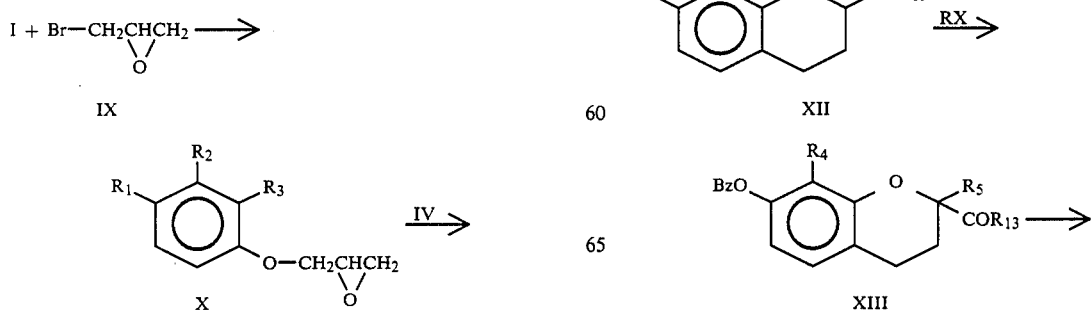

-continued
CHART B

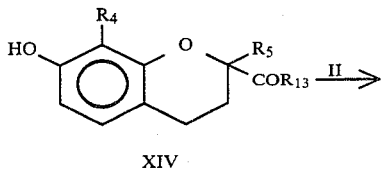

XIV

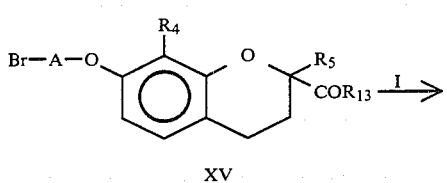

XV

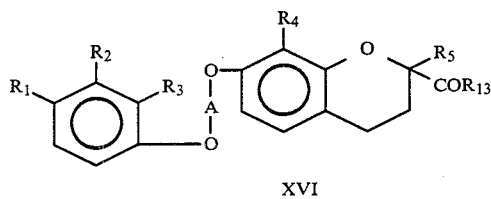

XVI

What is claimed is:
1. Compounds of the formula:

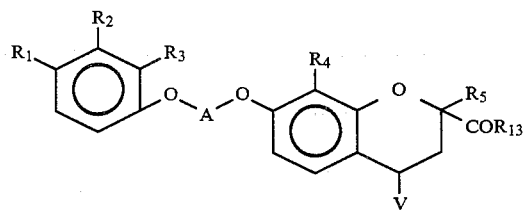

wherein A is a methylene chain having 1 to 10 carbon atoms inclusive, optionally substituted by hydroxy;
wherein V is:
 (a) hydrogen;
 (b) hydroxy; or
 (c) $R_6CH_2O$—;
wherein $R_1$ is:
 (a) —$COOH_3$;
 (b) —$CHOHCH_3$;
 (c) —$C_2H_5$;
 (d) -hydrogen; or
 (e) —$CO_2C_2H_5$
wherein $R_2$ is:
 (a) -hydrogen;
 (b) —OH; or
 (c) $R_{12}CH_2CO_2$—;

wherein $R_3$, $R_4$, $R_6$, $R_7$, $R_8$, $R_9$, $R_{10}$, $R_{11}$ and $R_{12}$ each of which may be the same or different, are:
 (a) hydrogen;
 (b) lower-alkyl having 1–6 carbon atoms inclusive; or
 (c) allyl;
wherein $R_5$ is:
 (a) hydrogen; or
 (b) $R_7CH_2C(O)$—;
wherein $R_{13}$ is hydrogen, hydroxy, alkoxy of 1 to 6 carbon atoms inclusive, or —OM wherein M is an alkali metal, alkyl of 1 to 6 carbon atoms, inclusive, or $NR_8 \oplus R_9 R_{10} R_{11}$, or $HNR_8 \oplus R_9 R_{10}$, or the pharmacologically acceptable addition salts thereof.

2. Compounds according to claim 1 wherein A is —$(CH_2)_5$— and V is hydroxy.

3. 7-[5-(2-n-propyl-3-hydroxy-4-acetylphenoxy)pentoxy]-4-hydroxy-8-n-propyl-chroman-2-carboxylic acid, a compound according to claim 2.

4. Compounds according to claim 1 wherein A is —$(CH_2)_5$— and V is hydrogen.

5. 7-[5-(2-n-propyl-3-hydroxy-4-acetylphenoxy)pentoxy]-8-n-propylchroman-2-carboxylic acid, a compound according to claim 4.

6. 7-[5-(2-n-propyl-3-hydroxy-4-ethylphenoxy)pentoxy]-8-n-propylchroman-2-carboxylic acid, a compound according to claim 4.

7. 7-[5-(2-n-propyl-4-carbomethoxyphenoxy)pentoxy]-8-n-propylchroman-2-carboxylic acid, a compound according to claim 4.

8. 2-carbomethoxy-7-[5-(2-n-propyl-3-hydroxy-4-acetylphenoxy)pentoxy]-8-n-propylchroman, a compound according to claim 4.

9. 2-carbomethoxy-7-[5-(2-n-propyl-3-hydroxy-4-ethylphenoxy)pentoxy]-8-n-propylchroman, a compound according to claim 4.

10. 2-carbomethoxy-7-[5-(2-n-propyl-4-carbomethoxyphenoxy)pentoxy]-8-n-propylchroman, a compound according to claim 4.

11. 2-formyl-7-[5-(2-n-propyl-3-hydroxy-4-acetylphenoxy)pentoxy-8-n-propylchroman, a compound according to claim 4.

12. A compound according to claim 1, wherein A is —$CH_2CHOHCH_2$— and V is hydrogen.

13. 7-[3-(2-n-propyl-3-hydroxy-4-acetylphenoxy)-2-hydroxypropoxy]-8-n-propylchroman-2-carboxylic acid, a compound according to claim 12.

14. Compounds according to claim 1 wherein A is —$(CH_2)_3$— and V is hydrogen.

15. 7-[2-(2-n-propyl-3-hydroxy-4-acetylphenoxy)propoxy]-8-n-propylchroman-2-carboxylic acid, a compound according to claim 14.

16. 2-carbomethoxy-7-[3-(2-n-propyl-3-hydroxy-4-acetylphenoxy)propoxy]-8-n-propylchroman, a compound according to claim 14.

17. 2-carbomethoxy-2-methyl-7-[3-(2-n-propyl-3-hydroxy-4-acetyl phenoxy)propoxy]-8-n-propylchroman, a compound according to claim 14.

* * * * *